US012403442B2

(12) United States Patent
Baumler

(10) Patent No.: US 12,403,442 B2
(45) Date of Patent: Sep. 2, 2025

(54) AMINE MODIFIED POLYSACCHARIDE URETHANE/UREA MICROCAPSULES

(71) Applicant: ENCAPSYS, LLC, Appleton, WI (US)

(72) Inventor: Stephen Baumler, Appleton, WI (US)

(73) Assignee: ENCAPSYS, LLC, Appleton, WI (US)

( * ) Notice: Subject to any disclaimer, the term of this patent is extended or adjusted under 35 U.S.C. 154(b) by 746 days.

(21) Appl. No.: 17/477,890

(22) Filed: Sep. 17, 2021

(65) Prior Publication Data
US 2022/0088558 A1 Mar. 24, 2022

Related U.S. Application Data

(60) Provisional application No. 63/217,931, filed on Jul. 2, 2021, provisional application No. 63/080,062, filed on Sep. 18, 2020.

(51) Int. Cl.
B01J 13/16 (2006.01)

(52) U.S. Cl.
CPC .................. B01J 13/16 (2013.01)

(58) Field of Classification Search
None
See application file for complete search history.

(56) References Cited

U.S. PATENT DOCUMENTS

| | | |
|---|---|---|
| 4,308,165 A | 12/1981 | Vassiliades et al. |
| 4,462,982 A | 7/1984 | Samejima et al. |
| 4,540,777 A | 9/1985 | Amort et al. |
| 5,545,483 A | 8/1996 | Bohland |
| 5,562,924 A | 10/1996 | Perrier et al. |
| 7,229,949 B2 | 6/2007 | Jadhav et al. |
| 7,951,390 B2 | 5/2011 | Jadhav et al. |
| 9,687,424 B2 | 6/2017 | Lei et al. |
| 10,143,632 B2 | 12/2018 | Dihora et al. |
| 10,385,296 B2 | 8/2019 | Song et al. |
| 10,537,503 B2 | 1/2020 | Lei et al. |
| 2005/0227906 A1 | 10/2005 | Schudel et al. |
| 2009/0274906 A1 | 11/2009 | Schwantes |
| 2010/0015430 A1 | 1/2010 | Hartmann et al. |
| 2011/0255156 A1 | 10/2011 | Jethmalani et al. |
| 2012/0276210 A1 | 11/2012 | Dihora et al. |
| 2013/0302392 A1 | 11/2013 | Mistry et al. |
| 2015/0158003 A1 | 6/2015 | Virgallito |
| 2016/0108340 A1 | 4/2016 | Feng et al. |
| 2016/0177241 A1 | 6/2016 | Brundel et al. |
| 2018/0015009 A1 | 1/2018 | Soubiran et al. |
| 2018/0042825 A1 | 2/2018 | Lei et al. |
| 2018/0215983 A1 | 8/2018 | Bardsley et al. |
| 2018/0369777 A1 | 12/2018 | Shi et al. |
| 2019/0231658 A1 | 8/2019 | Lei et al. |
| 2019/0269603 A1 | 9/2019 | Vigouroux |
| 2019/0275490 A1 | 9/2019 | Bachawala |
| 2020/0222873 A1* | 7/2020 | Neuman ............... A01N 25/28 |
| 2020/0406218 A1 | 12/2020 | Berthier et al. |
| 2021/0237020 A1* | 8/2021 | Bachawala .......... A23L 27/72 |
| 2022/0071863 A1* | 3/2022 | Xu ..................... A61K 8/817 |
| 2022/0087944 A1 | 3/2022 | Baumler |

FOREIGN PATENT DOCUMENTS

| | | |
|---|---|---|
| EP | 3170552 A1 | 5/2017 |
| EP | 3166580 B1 | 3/2020 |
| EP | 3819336 A1 | 5/2021 |
| WO | 9309176 A2 | 5/1993 |
| WO | 2014005779 A1 | 1/2014 |
| WO | 2014029695 A1 | 2/2014 |
| WO | 2016005250 A1 | 1/2016 |
| WO | 2017143174 A1 | 8/2017 |
| WO | 2020131855 A1 | 6/2020 |
| WO | 2020131866 A1 | 6/2020 |
| WO | 2020209907 A1 | 10/2020 |

OTHER PUBLICATIONS

International Search Report and Written Opinion for PCT/US2021/050857, Int'l PCT equivalent to instant application, dated Dec. 9, 2021.
International Search Report and Written Opinion for PCT/US2021/050779, Int'l PCT equivalent to companion application, dated Dec. 16, 2021.
Barclay, Thomas, et. al., "Review of polysaccharide particle-based functional drug delivery", Carbohydrate Polymers 221 (2019) pp. 94-112.
Namazi, N. et. al., "Hydrophobically modified starch using long-chain fatty acids for preparation of nanosized starch particles", Scientia Iranica C, 18(3), 439-445, 2011 DOI 10.1016/j.scient.2011.05.006.
Ye, F et. al., "Characterizations of oil-in-water emulsions stabilized by different hydrophobic maize starches". Carbohydr Polym. Jun. 15, 2017; 166; 195-201 DOI 10.1016/j.carbpol.2017.02.079.
Dokie, P et. al., "Colloid Charactistics and Emulsifying Properties of OSA Starches", Progr. Colloid Polym Sci (2008) 135:48-56 DOI 10.1007/2882_2008_116.
Shinetsu, Brochure entitled "Silicones for Resin Modification" 2011.
Copending unpublished U.S. Appl. No. 18/772,390, filed Jul. 15, 2024.
Copending unpublished U.S. Appl. No. 18/771,223, filed Jul. 12, 2024.
"Microcapsules prepared from starch derivatives," M. G Duarte et al., Journal of Materials Science: Materials in Medicine, vol. 8, Issue 5, pp. 321-323, May 1997.
"Controlled Release of Carboxylic-Containing Herbicides by starch-g-poly(butyl)acrylate," Zhifeng Zhu et al.; Journal of Applied Polymer Science, Vo.81, Issue 6, pp. 1535-1543, Aug. 8, 2001.
"A new biodegradable plastic made from starch graft poly(methyl acrylate) copolymer," Ronald J Dennenberg et al.; Journal of Applied Polymer Science, Vo. 22, Issue 2, pp. 459-465, Feb. 1978.

(Continued)

Primary Examiner — Jeffrey D Washville

(74) Attorney, Agent, or Firm — Hoffmann & Baron, LLP; Ed Welch

(57) ABSTRACT

Core shell microcapsules are provided wherein the capsule shell is an interfacial copolymer formed of an amine modified polysaccharide cross-linked with an isocyanate.

36 Claims, No Drawings

(56) References Cited

OTHER PUBLICATIONS

"Comparison of poly(acryl starch) and poly(lactide-co-glycolide) microspheres as drug delivery system for a rotavirus vaccine," Cecilia Sturesson et al., Journal of Controlled Release, vol. 68, Issue 3, pp. 451-450, Sep. 3, 2000.

"Starch-Based Hydrogels: Present Status and Applications," Hanafi Ismail et al., School of Materials and Mineral Resources Engineering, Universiti Sains Malaysia, Penang, Malaysia: published in International Journal of Polymeric Materials and Polymeric Biomaterials, vol. 62, Issue 7, pp. 411-420,(2013).

"Multifunctional Starch Derivatives: Synthesis, Characterization and Properties,". Amma M.L. Huijbrechts, Doctoral Thesis, Wageningen University, Wageningen, The Netherlands (2008), ISBN: 978-90-8585-250-6.

* cited by examiner

AMINE MODIFIED POLYSACCHARIDE URETHANE/UREA MICROCAPSULES

RELATED APPLICATIONS

The present application claims the benefit of prior U.S. Provisional Patent Application Nos. 63/217,931, filed Jul. 2, 2021, entitled "Amine Modified Polysaccharide Urethane/Urea Microcapsules" and 63/080,062, filed Sep. 18, 2020, entitled "Multifunctional (Meth)acrylate Polysaccharide Microcapsules", the contents of both of which are hereby incorporated herein by reference in their entirety.

FIELD

The present teaching relates to capsule manufacturing processes and microcapsules produced by such processes, along with improved articles of manufacture based on such microcapsules.

DESCRIPTION OF THE RELATED ART

Various processes for microencapsulation, and exemplary methods and materials are set forth in various patents, such as Schwantes (U.S. Pat. No. 6,592,990), Nagai et al. (U.S. Pat. No. 4,708,924), Baker et al. (U.S. Pat. No. 4,166,152), Wojciak (U.S. Pat. No. 4,093,556), Matsukawa et al. (U.S. Pat. No. 3,965,033), Matsukawa (U.S. Pat. No. 3,660,304), Ozono (U.S. Pat. No. 4,588,639), Irgarashi et al. (U.S. Pat. No. 4,610,927), Brown et al. (U.S. Pat. No. 4,552,811), Scher (U.S. Pat. No. 4,285,720), Hayford (U.S. Pat. No. 4,444,699), Shioi et al. (U.S. Pat. No. 4,601,863), Kiritani et al. (U.S. Pat. No. 3,886,085), Jahns et al. (U.S. Pat. Nos. 5,596,051 and 5,292,835), Matson (U.S. Pat. No. 3,516,941), Chao (U.S. Pat. No. 6,375,872), Foris et al. (U.S. Pat. Nos. 4,001,140; 4,087,376; 4,089,802 and 4,100,103) and Greene et al. (U.S. Pat. Nos. 2,800,458; 2,800,457 and 2,730,456), among others and as taught by Herbig in the chapter entitled "Microencapsulation" in Kirk-Othmer Encyclopedia of Chemical Technology, V. 16, pages 438-463.

Other useful methods for microcapsule manufacture are: Foris et al. (U.S. Pat. Nos. 4,001,140 and 4,089,802) describing a reaction between urea and formaldehyde; Foris et al. (U.S. Pat. No. 4,100,103) describing reaction between melamine and formaldehyde; and Fuji Photo Film Co, (GB No. 2,062,570) describing a process for producing microcapsules having walls produced by the polymerization of melamine and formaldehyde in the presence of a styrene sulfonic acid. Alkyl acrylate-acrylic acid copolymer capsules are taught in Brown et al. (U.S. Pat. No. 4,552,811). Each patent described throughout this application is incorporated herein by reference to the extent each provides guidance regarding microencapsulation processes and materials.

Interfacial polymerization is a process wherein a microcapsule wall of polyamide, an epoxy resin, a polyurethane, a polyurea or the like is formed at an interface between two phases. Riecke (U.S. Pat. No. 4,622,267) discloses an interfacial polymerization technique for preparation of microcapsules in which the core material is initially dissolved in a solvent and an aliphatic diisocyanate soluble in the solvent mixture is added. Subsequently, a nonsolvent for the aliphatic diisocyanate is added until the turbidity point is just barely reached. This organic phase is then emulsified in an aqueous solution, and a reactive amine is added to the emulsion. The amine diffuses to the interface, where it reacts with the diisocyanate to form polymeric polyurethane shells. A similar technique, used to encapsulate salts which are sparingly soluble in water in polyurethane shells, is disclosed in Greiner et al. (U.S. Pat. No. 4,547,429). Matson (U.S. Pat. No. 3,516,941) teaches polymerization reactions in which the material to be encapsulated, the "core material," is dissolved in an organic, hydrophobic oil phase which is dispersed under high shear mixing in an aqueous phase to form a dispersion of fine oil droplets. The aqueous phase has dissolved therein aminoplast precursor materials, namely, an amine and an aldehyde, which upon polymerization form the wall of the microcapsule. Polymerization is initiated by the addition and initiation of an acid catalyst which results in the formation of an aminoplast polymer which is insoluble in both phases. As the polymerization advances, the aminoplast polymer separates from the aqueous phase and deposits on the surface of the dispersed droplets of the oil phase where polymerization continues to form a capsule wall at the interface of the two phases, thus encapsulating the core material. Urea-formaldehyde (UF), urea-resorcinol-formaldehyde (URF), urea-melamine-formaldehyde (UMF), and melamine-formaldehyde (MF), capsule formations proceed in a like manner. Depending upon the selection of wall forming materials and the encapsulation steps chose, oftentimes each phase, the oil phase and the water phase, contains at least one of the capsule wall-forming materials wall and polymerization occurs at the phase boundary. Thus, a polymeric capsule shell wall forms at the interface of the two phases thereby encapsulating the core material. Wall formation of polyester, polyamide, and polyurea capsules also typically proceed via interfacial polymerization.

One common microencapsulation processes can be viewed as a series of steps. First, the core material which is to be encapsulated is typically emulsified or dispersed in a suitable dispersion medium. This medium is typically aqueous but involves the formation of a polymer rich phase. Most frequently, this medium is a solution of the intended capsule wall forming material, or at least one component thereof. The solvent characteristics of the medium are changed such as to cause phase separation of the wall forming material whereby the wall forming material is contained in a discrete liquid phase which is also dispersed in the same medium as the intended capsule core material. The dispersed droplets of the wall forming material deposit themselves as a continuous coating on the surface of the dispersed droplets of the internal phase or core material. The wall forming material is then solidified. This process is commonly known as coacervation.

Turning to the present teaching the use of starches in microencapsulation is well known. For example, Li, Jason Z., "The Use of Starch-Based Materials for Microencapsulation" (chapter 18), in Gaonkar, et. al., (Eds), Microencapsulation in the Food Industry, DOI: http: dx.doi.org/10.1016//B978-0-12-404568-2.00018-2, provides an overview of starch-based materials used in microencapsulation including the modification thereof to alter their hydrophilic and hydrophobic properties.

Vassiliades et. al. (U.S. Pat. No. 4,138,362) describe various microcapsules subsequently treated with starch as a binder for adhering the microcapsules to substrates Following on the foregoing, Vassiliades et. al. (U.S. Pat. No. 4,308,165) describe microcapsules formed of a polyfunctional isocyanate cross-linking agent with an aqueous solution of an emulsifying agent comprising starch having ether-linked aralkyl groups.

Bohland (U.S. Pat. No. 5,545,483) describes polyamide microcapsule formed in the presence of a starch emulsifier, subsequently coated with an isocyanate emulsion to reduce microcapsule yellowing and decrease microcapsule permeability.

Jadhav et al. (U.S. Pat. No. 7,951,390) describe a microcapsule for agricultural applications based on various starches and starch derivatives cross-linked with vinyl monomers such as methyl methacrylate or other lower alkyl acrylates.

Lei et. al. (U.S. Publ. Pat. Appl. No. 20180042825) disclose polyurea and polyurethane microcapsules formed in the presence of various emulsifiers including select starches as well the coating of the so formed microcapsules with various deposition aids/binders including various starches.

Despite all the improvements and advances in microencapsulation technology, both from a processing and compositional standpoint, there is still a need for further improvements, particularly with respect to the simplification/efficacy of the microencapsulation process, microcapsule wall performance and durability, microcapsule adherence and deposition, and, most especially, the degradability of the microcapsules.

SUMMARY

The present teaching relates to a microcapsule formed by any suitable oil-in-water microencapsulation process, especially interfacial polymerization, comprising a core material and a shell encapsulating the core material wherein the shell comprises the reaction product of a) an amine modified polysaccharide, preferably an amine modified, hydrophobically modified polysaccharide, especially an amine modified, esterified polysaccharide, derived from a water phase and b) an isocyanate, preferably one or more di- and/or poly-isocyanates, preferably and/or predominantly di-isocyanates, derived from an oil phase. Optionally, the water phase may also contain amine-free polysaccharides. Preferably the amine modified polysaccharide is a starch, especially a hydrophobically modified starch, e.g., an esterified starch, which has been reacted to add amino functionality to the starch, most especially by reaction with one or more amino-silanes, amino-(meth)acrylates, and/or amine radical initiators or a combination of any two or more of the foregoing. The amino functional group can be selected from primary amine, secondary amine, amide, or an amidine group. The resulting microcapsules comprise cross-linked polyurethanes and/or polyureas, most typically polyurethane/ureas.

The microcapsules of the present teaching are formed in either a one-step oil-in-water process or a two-step oil-in-water process. In the former, the amine modified polysaccharide is a preformed material which is dispersed in the water phase. In the latter, the amine modified polysaccharide is formed as a first step, generally without isolation, in the water phase, either before or after the addition of the isocyanate containing oil phase, most preferably before so as to avoid any substantial reaction between the isocyanate and the reactants for the amine modified polysaccharide. If after the addition of the isocyanate, it is preferable that the reaction conditions for the formation of the amine modified polysaccharide are such as not to induce or induce any substantial reaction of the amine reactants with the isocyanate, as evidenced by the presence of cross-linked polymer at the interface of the water and oil phases, especially as evidenced by partial wall formation.

The amine modified polysaccharide will generally be prepared or have been prepared by reacting the polysaccharide with the amine reactant in a mole ratio sufficient to substitute from 0.005 up to 8 mole percent, preferably from 0.01 up to 6 mole percent, more preferably from 0.05 up to 4 mole percent of the hydroxy groups of the polysaccharide with a moiety having a free or reactive amino group, provided that, in the case wherein the amine modified polysaccharide is a maltodextrin, the amine modified polysaccharide has at least 1, preferably at least 2, more preferably at least 4 amino functional groups per molecule. Furthermore, should it be desired, one may add additional polysaccharide (free of amine modification) to the water phase (after preparation of the amine modified polysaccharide, as appropriate). In forming the microcapsules, the weight ratio of the total wall forming polysaccharide content (e.g., the combination of the amine modified polysaccharide and the amine-free polysaccharide, if present,) to isocyanate is generally from 40:60 to 99:1; preferably 50:50 to 99:1, more preferably from 60:40 to 98:2; most preferably from 70:30 to 98:2.

The core material typically and preferably comprises a benefit agent. Exemplary benefit agents include perfumes, fragrances, agricultural actives, phase change materials, essential oils, lubricants, colorants, preservatives, antimicrobial actives, antifungal actives, herbicides, antiviral actives, antiseptic actives, antioxidants, biological actives, deodorants, antiperspirant actives, emollients, humectants, exfoliants, ultraviolet absorbing agents, corrosion inhibitors, silicone oils, waxes, bleach particles, fabric conditioners, malodor reducing agents, dyes, optical brighteners and mixtures thereof.

According to second aspect of the present teaching there is provided a one-step oil-in water microencapsulation process for the of formation of the aforementioned microcapsules. Generally speaking, there is provided an oil-in-water microencapsulation process wherein an oil phase comprising a core material and an isocyanate wall forming material, preferably a di- and/or poly-isocyanate, is dispersed in an aqueous phase comprising an amine modified polysaccharide wall forming material, preferably an amine modified, hydrophobically modified polysaccharide, which dispersion is then subjected to polymerization conditions whereby the isocyanate and the amine modified polysaccharide form a cross-linked shell wall. Specifically, there is provided a microencapsulation process which entails a) forming an oil phase of the core material and an isocyanate, especially a di- and/or poly-isocyanate, monomer, dimer, trimer or biuret or a urethane or urea prepolymer or oligomer prepared therefrom, b) forming an aqueous phase of water and the amine modified polysaccharide, and, optionally, an emulsifier and/or initiator, c) dispersing/emulsifying the oil phase into the water phase under high shear agitation to form an oil-in-water emulsion comprising droplets of the oil phase dispersed in the water phase; and d) effecting polymerization of the wall forming materials, e.g., by heat and/or activation of the initiator, if present, thereby forming a polymer shell surrounding the droplets of the emulsion. The amine modified polysaccharide is preferably an amine modified maltodextrin or an amine modified starch, especially an amine modified, hydrophobically modified starch, e.g., an esterified starch, which has been aminated or reacted with a suitable amine or aminating agent to add amino functionality to the maltodextrin or starch, most especially by reaction with one or more amino-silanes, amino-(meth)acrylates, and/or amine radical initiators or a combination of any two or more of the foregoing. The amino functional group can be selected from a primary amino, secondary amino, amide, or an amidino group. The amine modified polysaccharide will generally have been prepared by having reacted the polysaccharide with the amine reactant in a mole ratio sufficient to substitute from 0.005 up to 8 mole percent, preferably from 0.01 up to 6 mole percent, more preferably from 0.05 up to 4 mole percent of the hydroxy groups of the polysaccharide with a moiety having a free or reactive amino group, provided that, in the case wherein the amine modified polysaccharide is a maltodextrin, the amine modified polysaccharide has at least 1, preferably at least 2, more preferably at least 4 amino functional groups per molecule. Furthermore, should it be desired, one may add additional polysaccharide (free of amine modification) to the water phase (after preparation of the amine modified polysaccharide, as appropriate). In forming the microcapsules, the weight ratio of the total wall forming polysaccharide content (e.g., the combination of the amine modified polysaccharide and the amine-free polysaccharide, if present,) to isocyanate is generally from 40:60 to 99:1; preferably 50:50 to 99:1, more preferably from 60:40 to 98:2; most preferably from 70:30 to 98:2.

According to a third aspect of the present teaching there is provided a two-step oil-in water microencapsulation process for the of formation of the aforementioned microcapsules. Generally speaking, there is provided an oil-in-water microencapsulation process wherein a first step comprises the preparation of an amine modified polysaccharide, preferably an amine modified, hydrophobically modified polysaccharide, followed by a second step wherein a microcapsule wall is formed from the reaction of the amine modified polysaccharide and an isocyanate, preferably a di- or poly-isocyanate. Specifically, there is provided a microencapsulation process wherein a) a water phase is prepared by combining a polysaccharide and an amine co-reactive therewith or a suitable aminating agent, especially one or more aminosilanes, amino-(meth)acrylates, and/or amine radical initiators, in water, b) forming an oil phase comprising a core material and an isocyanate wall forming material, preferably a di- and/or poly-isocyanate, c) either i) subjecting the water phase composition to reaction conditions whereby the amine modified polysaccharide is formed and subsequently dispersing the oil phase in the water phase or ii) dispersing the oil phase in the water phase and subsequently subjecting the dispersion to reaction conditions whereby the amine modified polysaccharide is formed, and, thereafter, d) subjecting the dispersion to polymerization conditions whereby the isocyanate and the amine modified polysaccharide form a cross-linked polymer, e.g., by heat and/or activation of the initiator, if present, thereby forming a polymer shell surrounding the droplets of the emulsion. The water phase preferably includes a caustic agent, preferably caustic soda, to aid in the reaction of the polysaccharide and the aminating agent or reactant. Additionally, the water phase may also include an emulsifier and/or initiator to aid in the microencapsulation, which may be added prior to or subsequent to the amination process. Preferably, the isocyanate is a di- and/or poly-isocyanate monomer, dimer, trimer or biuret or a urethane or urea prepolymer or oligomer prepared therefrom, most preferably, the isocyanate is one more di-isocyanates or predominantly di-isocyanates. Similarly, the polysaccharide is preferably a starch or a maltodextrin, more preferably a hydrophobically modified polysaccharide, especially a hydrophobically modified maltodextrin or starch, most preferably a hydrophobically modified starch. Although it is preferable to start with a hydrophobically modified polysaccharide, especially a hydrophobically modified starch, it is also to be appreciated that hydrophobic modification of the polysaccharide may be an additional step of the present process whereby the hydrophobizing agent, especially the ester, employed to add hydrophobicity to the polysaccharide, is reacted with the polysaccharide prior to, concurrent with or subsequent to the amine modification of the polysaccharide. As noted, the amine modified polysaccharide is preferably reacted with one or more aminosilanes, amino-(meth)acrylates, and/or amine radical initiators or a combination of any two or more of the foregoing. The amine functional group can be selected from primary amine, secondary amine, amide, or an amidine group.

Generally speaking, the amine modified polysaccharide will be prepared by reacting the polysaccharide with the amine or aminating reactant in mole ratio sufficient to substitute from 0.005 up to 8 mole percent, preferably from 0.01 up to 6 mole percent, more preferably from 0.05 up to 4 mole percent of the hydroxy groups of the polysaccharide with a moiety having a free or reactive amino group, provided that, in the case wherein the amine modified polysaccharide is a maltodextrin, the amine modified polysaccharide has at least 1, preferably at least 2, more preferably at least 4 amino functional groups per molecule. Furthermore, should it be desired, one may add additional polysaccharide (free of amine modification) to the water phase (after preparation of the amine modified polysaccharide, as appropriate). In forming the microcapsules, the weight ratio of the total wall forming polysaccharide content (e.g., the combination of the amine modified polysaccharide and the amine-free polysaccharide, if present,) to isocyanate is generally from 40:60 to 99:1; preferably 50:50 to 99:1, more preferably from 60:40 to 98:2; most preferably from 70:30 to 98:2.

According to a fourth aspect of the present teaching there is provided polyurea/polyurethane microcapsules formed of a) polysaccharides, preferably hydrophobically modified polysaccharides, especially esterified polysaccharides, b) isocyanates, preferably one or more di- and/or poly-isocyanates, preferably and/or predominantly di-isocyanates, and c) one or more di- or poly-functional aminating agents having at least one amine or amino functionality, especially, one or more aminosilanes, amino-(meth)acrylates, and/or amine radical initiators or a combination of any two or more of the foregoing, wherein the weight ratio of the wall forming polysaccharide content to isocyanate is generally from 40:60 to 99:1; preferably 50:50 to 99:1, more preferably from 60:40 to 98:2; most preferably from 70:30 to 98:2 and the mole ratio of the amine or aminating agent to the isocyanate of from 7:1 to 1:7, preferably from 5:1 to 1:5, more preferably 3:1 to 1:3: though, in the case of maltodextrins, especially low molecular weight maltodextrins, the mole ratio of amine or aminating agent to isocyanate may be up to 10:1, even up to 15:1, or more.

According to a fifth aspect of the present teaching there is provided a one-step oil-in water microencapsulation process for the of formation of the microcapsules according to the fourth aspect wherein an oil phase composition comprising a core material and an isocyanate wall forming material, preferably a di- and/or poly-isocyanate, is dispersed in an aqueous phase composition comprising a polysaccharide wall forming material, preferably a hydrophobically modified polysaccharide, and a di- or polyfunctional amine or aminating agent reactive with both the polysaccharide and the isocyanate, which dispersion is then subjected to polymerization conditions whereby the isocyanate, the polysaccharide and the amine or aminating agent agent form a shell wall. Specifically, there is provided a microencapsulation process which entails a) forming an oil phase of the core material and an isocyanate, especially a di- and/or poly-isocyanate monomer, dimer, trimer or biuret or a urethane or urea prepolymer or oligomer prepared therefrom, b) forming an aqueous phase of i) water, ii) a polysaccharide, especially a hydrophobically modified polysaccharide, iii) one or more di- or poly-functional amines or aminating agents having at least one amine or amino functionality, especially, one or more aminosilanes, amino-(meth)acrylates, and/or amine radical initiators or a combination of any two or more of the foregoing, and iv) optionally, though preferably, a caustic agent, especially caustic soda, and v) optionally, an emulsifier and/or initiator, c) dispersing/emulsifying the oil phase into the water phase under high shear agitation to form an oil-in-water emulsion comprising droplets of the oil phase dispersed in the water phase; and d) effecting polymerization of the wall forming materials, e.g., by heat and/or activation of the initiator, if present, thereby forming a polymer shell surrounding the droplets of the emulsion. The polysaccharide is preferably hydrophobically modified polysaccharide, especially a maltodextrin or starch, more preferably a hydrophobically modified starch, e.g., an esterified starch. The amine or aminating agent has at least one reactive amine or amino functionality and is at least di-functional so as to be reactive with both the isocyanate and the polysaccharide: though preferably the functionality is of the amine or aminating agent is no more than 6, preferably no more than 4, most preferably no more than 3. The amine functional group can be selected from primary amine, secondary amine or an amidine group. Generally, the weight ratio of the wall forming polysaccharide content to isocyanate is generally from 40:60 to 99:1; preferably 50:50 to 99:1, more preferably from 60:40 to 98:2; most preferably from 70:30 to 98:2 and the mole ratio of the amine or aminating agent to the isocyanate is from 7:1 to 1:7, preferably from 5:1 to 1:5, more preferably 3:1 to 1:3: though, in the case of maltodextrins, especially low molecular weight maltodextrins, the mole ratio of amine or aminating agent to isocyanate may be up to 10:1, even up to 15:1, or more.

Finally, according to a sixth embodiment there are provided articles of manufacture incorporating the aforementioned microcapsules. Exemplary articles of manufacture include, but are not limited to soaps, surface cleaners, laundry detergents, fabric softeners, shampoos, textiles, paper products including tissues, towels, napkins, and the like, adhesives, wipes, diapers, feminine hygiene products, facial tissues, pharmaceuticals, deodorants, heat sinks, foams, pillows, mattresses, bedding, cushions, cosmetics and personal care products, medical devices, packaging, agricultural products, coolants, wallboard, insulation, and the like.

The microcapsules formed according to the present teaching provide i) improved properties, both in terms of physical properties and performance, such as shell strength, integrity and leakage, ii) the ability to protect, retain or deliver a benefit agent to a targeted situs and/or on a controlled basis, and/or iii) improved degradability. Indeed, forming robust microcapsules based at least in part on natural, renewable or sustainable components continues to be an unmet need. The present teaching advances the art by teaching such microcapsules and their process of manufacture as well as articles beneficially employing such microcapsules.

DETAILED DESCRIPTION

As used in the present specification and claims, reference to "amine modified polysaccharide" and "amine modified starch" or like designation means that the polysaccharide or starch, respectively, has been aminated or reacted with a multifunctional amine whereby the resulting polysaccharide or starch has one or more, preferably a plurality of, amino functionality or groups. Similarly, reference to "hydrophobically modified polysaccharide" and "hydrophobically modified starch" or like designation means that the polysaccharide or starch, respectively, has been reacted or altered to alter its hydrophobic lipophilic balance (HLB) number to fall within the range of from 9-18. Most often, as discussed below, this modification is accomplished by esterification. Additionally, the term (meth)acrylate is intended to refer to the acrylate and its corresponding methacrylate. Finally, although reference is made to starches specifically throughout the specification, this is done as a matter of convenience, particularly since it is the most preferred polysaccharide; however, as context allows, the term is to be understood as referring to polysaccharides generally and especially to the starches and maltodextrins specifically.

The present teaching generally relates to select microcapsules formed by any suitable oil-in-water microencapsulation process, especially an interfacial polymerization process, comprising a core material and a shell encapsulating the core material wherein the shell comprises the reaction product of a) polysaccharide, preferably a hydrophobically modified polysaccharide, especially an esterified polysaccharide, b) an isocyanate, preferably one or more di- and/or poly-isocyanates, preferably and/or predominantly di-isocyanates, and c) one or more di- or poly-functional amines or aminating agents, especially, one or more amino-silanes, amino-(meth)acrylates, and/or amine radical initiators or a combination of any two or more of the foregoing, wherein the mole ratios of the components are within specific ranges in order to achieve the microcapsules of the desired properties. In one embodiment the three key wall forming reactants, (a) to (c) above, are co-reacted whereby the so-formed cross-linked polyurethane/polyurea polymer shell is a random polymer. In the preferred embodiment the shell wall formation is more controlled and of a more defined structure: specifically, the polysaccharide and the amine or aminating agent are pre-reacted to form an amino functional or amine modified polysaccharide which is subsequently reacted with the isocyanate to form the cross-linked polyurethane/polyurea shell wall.

Important, if not critical, to the performance and beneficial properties of the microcapsules is the weight and/or mole ratios of the key wall forming reactants, (a) to (c). Specifically, in the case of the aforementioned random polymer shell walls, the mole ratio of the amine or aminating agent to the isocyanate is from 7:1 to 1:7, preferably from 5:1 to 1:5, more preferably 3:1 to 1:3: though, in the case of maltodextrins, especially low molecular weight maltodextrins, the mole ratio of amine or emanating agent to isocyanate may be up to 10:1, even up to 15:1 or more and the weight ratio of the polysaccharide content to isocyanate is generally from 40:60 to 99:1; preferably 50:50 to 99:1, more preferably from 60:40 to 98:2; most preferably from 70:30 to 98:2.

As noted, the preferred microcapsules are formed of an amine modified polysaccharide and the isocyanate, optionally in the presence of a polysaccharide which is free of amino functionality. The amine modified polysaccharide may be pre-formed, with or without isolation or purification, and added to the reaction mix or it may be formed as a step in the microencapsulation process itself, both as described further below. If additional, amine-free polysaccharide is to be added, it should be added to the water phase after preparation of the amine modified polysaccharide in the case of the microcapsules formed by the two-step process. In forming the amine modified polysaccharide the mole ratio of the polysaccharide to amine or aminating agent is sufficient to substitute from 0.005 up to 8 mole percent, preferably from 0.01 up to 6 mole percent, more preferably from 0.05 up to 4 mole percent of the hydroxy groups of the polysaccharide with a moiety having a free or reactive amino group, provided that, in the case of the maltodextrins, the amine modified polysaccharide has at least 1, preferably at least 2, more preferably at least 4 amino functional groups per molecule. Additionally, the mole ratio of the total polysaccharide content (amine modified and amine free) to isocyanate is generally from 40:60 to 99:1; preferably 50:50 to 99:1, more preferably from 60:40 to 98:2; most preferably from 70:30 to 98:2. Although not directly co-reacted in these embodiments, a good rule of thumb for achieving or assessing whether one will attain the aforementioned degree of amine substitution of the polysaccharide is to design the protocol for the production of the microcapsules such that the mole ratio of the amine or aminating agent used in the modification of the polysaccharide to the isocyanate used in the production of the microcapsules is from 7:1 to 1:7, preferably from 5:1 to 1:5, more preferably 3:1 to 1:3: though, in the case of maltodextrins, especially low molecular weight maltodextrins, the mole ratio of amine or emanating agent to isocyanate may be up to 10:1, even up to 15:1 or more.

Polysaccharides

The first wall forming component of the microcapsules according to the present teaching is the polysaccharide component. Suitable polysaccharides include homopolysaccharides and heteropolysaccharides, linear polysaccharides and branched polysaccharides, all of which are water soluble or sufficiently water soluble in the water phase at the levels used. Preferred polysaccharides are the maltodextrins and starches, especially the modified maltodextrins and modified starches, most especially the hydrophobically modified maltodextrins and starches. Suitable maltodextrins generally correspond in structure to that shown in Formula I,

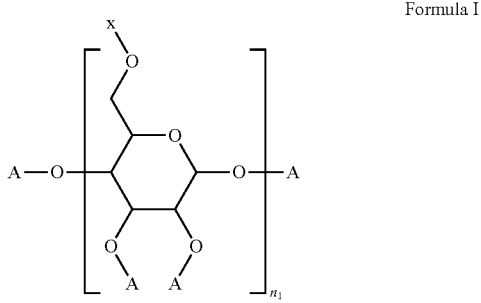

Formula I wherein $n_1$ is an integer from 2 to 40 and x is a terminal hydrogen or, rarely, up to several repeat glucose units, and each A is independently a terminal hydrogen or an addict corresponding to the nature of the modification of the maltodextrin, in the case of maltodextrins. Starches, on the other hand, are much higher molecular weight structures, again corresponding to Formula 1, typically comprising 0 to 30% amylose and 70 to 100% amylopectin: the higher amylopectin content corresponding to waxy starches. Amylose corresponds to the structure of Formula 1 wherein $n_1$ is from 200 to several thousand, typically up to 3000 and x is a terminal hydrogen or, rarely, up to several repeat glucose units. Amylopectin, on the other hand, is a highly branched structure wherein x corresponds to the structure within the brackets of Formula 1 with multiple branches extending from the main branch and the sub branches, each having multiple repeating units corresponding to Formula 1. Amylopectin typically has several thousand to several hundred thousand repeat glucose units, typically 2000 to 200,000, preferably 2000 to 100,000, more preferably 3000 to 20,000. Again, with respect to the starches, each A is independently a terminal hydrogen or an adduct corresponding to the nature of the modification of the starch.

Modification of the maltodextrins and starches are well known and widely available. Exemplary modifications, especially of the starches, are those wherein the material to be modified is acid-modified by treatment with hydrochloric acid or sulfuric acid or both, bleached, oxidized by treatment with chlorine or sodium hypochlorite, esterified, etherified, esterified and etherified, enzymatically treated, and the like. Especially preferred modified starches are those that are esterified, etherified, and/or treated enzymatically as described in, for example, Li, Jason Z., "The Use of Starch-Based Materials for Microencapsulation" (chapter 18), in Gaonkar, et. al., (Eds), Microencapsulation in the Food Industry, DOI: http: dx.doi.org/10.1016//B978-0-12-404568-2.00018-2, which is hereby incorporated herein by reference. An especially preferred class of modified starch is that of the esterified starches, such as octenyl succinic anhydride modified starch. While unmodified starches can be used, it is preferable to use modified polysaccharides since such modification is capable of changing the natural hydrophilic/lipophilic properties of the native starch, making them more suitable and efficacious for use in the microencapsulation process as well as in providing additional benefits to the resultant microcapsules.

As noted above, the preferred polysaccharides for use in the practice of the present teaching are the maltodextrins and starches, particularly the esterified starches, most preferably the hydrophobically modified starches which are herein characterized as esterified starches having an HLB value of from 9 to 18. Hydrophobically modified starches and their preparation are well known and widely practiced and commercially available. Typically, hydrophobic modification is attained by esterification with acid anhydrides, fatty acids and fatty acid chlorides, especially fatty acid substituted acid anhydrides, long chain fatty acids and long chain fatty acid chlorides. Especially preferred are the $C_6$ to $C_{24}$, preferably $C_8$ to $C_{18}$, fatty acids and fatty acid chlorides and fatty acid substituted succinic anhydride: though short chain fatty acids and short chain fatty acid chlorides are also useful. Exemplary fatty acids and their corresponding acid chlorides include the following fatty acids: lauric, palmitic, stearic, oleic, caprylic, butyric, succinic, octenyl succinic, dodecenyl succinic, and the like. Exemplary acid anhydrides include octenyl succinic anhydride and dodecyl succinic anhydride. Various reaction processes and conditions are known and may involve treatment of the starch in the presence of dicyclohexyl carbodiimide (DCC), dimethylaminopyridine (DMAP), lithium chloride, dimethylacetamide (DMAC) and combinations of two or more of the foregoing, typically in the presence of a solvent or an alkali reaction medium. See, e.g., Amort et. al. (U.S. Pat. No. 4,540,777); H. Namazi et. al., "Hydrophobically Modified Starch Using Long-Chain Fatty Acids for Preparation of Nanosized Starch Particles", Scientia Iranica C, 18(3), 2011 pp. 439-445; J. M. Fang et. al., "The Preparation and Characterisation of a Series of Chemically Modified Potato Starches". Carbohydrate Polymers, 47(3), Feb. 15, 2002, pp. 245-252; and A. Besheer et. al., "Hydrophobically Modified Hydroxyethyl Starch: Synthesis, Characterization, and Aqueous Self-Assembly into Nano-sized Polymeric Micelles and Vesicles, all of which are incorporated herein by reference in their entirety.

Isocyanate

The second wall forming component of the microcapsules of the present teaching is the isocyanate. As used herein the term "isocyanate" is used interchangeably with the term "polyisocyanate" and refers to such materials having two or more isocyanate groups, i.e., —N═C═O. Although mono-isocyanates may be used in combination with the herein recited isocyanates, the critical and required isocyanates have at least two isocyanate groups: preferably, the isocyanates are wholly or predominantly di-isocyanates: at least 50 mole percent, preferably at least 65 mole percent, most preferably at least 75 mole percent. Suitable isocyanates can be aromatic, aliphatic, linear, branched, or cyclic. They include the monomeric, dimer, trimer, biuret forms as well as oligomers and prepolymers thereof, especially oligomers and prepolymers thereof with other compounds reactive with the isocyanate groups (i.e., —N═C═O), e.g., diols, diamines, and the like. Preferably, the isocyanate is a diisocyanate or a combination thereof with mono-, tri- or tetra- or higher isocyanates. Generally, the isocyanate contains, on average, 2 to 4 isocyanate groups; though for particular embodiments it is desirable to use or include isocyanates containing at least three isocyanate functional groups. Furthermore, depending upon the application, it is desirable to use combinations of aliphatic and aromatic isocyanates.

Suitable aliphatic isocyanates include hexamethylene diisocyanate, dicyclohexyl-methyl diisocyanate, isophorone diisocyanate, as well as their respective trimers and biurets such as the trimer of hexamethylene diisocyanate, the trimer of isophorone diisocyanate and the biuret of hexamethylene diisocyanate. Exemplary commercially available aliphatic isocyanates include, e.g., DESMODUR W which is dicyclohexylmethane diisocyanate; DESMODUR N3600, DESMODUR N3700, and DESMODUR N3900, which are low viscosity, polyfunctional aliphatic polyisocyanates based on hexamethylene diisocyanate; and DESMODUR 3600 and DESMODUR N100 which are aliphatic polyisocyanates based on hexamethylene diisocyanate, each of which is available from Covestro AG.

Suitable aromatic isocyanates include those having phenyl, tolyl, xylyl, naphthyl or diphenyl moiety as the aromatic component. Exemplary aromatic isocyanates include a polyisocyanurate of toluene diisocyanate, a trimethylol propane-adduct of toluene diisocyanate or a trimethylol propane-adduct of xylylene diisocyanate. One class of suitable aromatic isocyanates are the polyisocyanates having the generic structure:

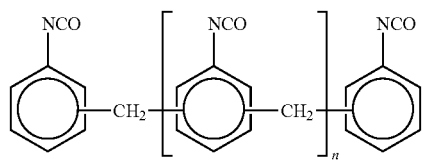

(i.e., polymeric methylene diphenyl diisocyanate or PMDI, and its structural isomers) wherein n can vary from zero to a desired number, preferably n is less than 6. Mixtures of these polyisocyanate are also suitable wherein the value of n can vary from 0 to 6 with an average value of n falls in between 0.5 and 1.5.

Specific examples of wall forming monomer isocyanates include, for example, 1,5-naphthylene diisocyanate, 4,4'-diphenylmethane diisocyanate (MDI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenyl-methane diisocyanate. 4,4'-dibenzyl diisocyanate, 1,3-phenylene diisocyanate, 1,4-phenylene diisocyanate, the isomers of toluene diisocyanate (TDI), optionally in a mixture, 1-methyl-2,4-diisocyanato-cyclohexane, 1,6-diisocyanato-2,2,4-trimethyl-hexane, 1,6-diisocyanato-2,4,4-trimethylhexane, 1-isocyanatomethyl-3-isocyanato-1,5,5-trimethylcyclohexane, 4,4'-diisocyanatophenylperfluoroethane, tetramethoxybutane 1,4-diisocyanate, butane 1,4-diisocyanate, chlorinated and brominated diisocyanates, phosphorus-containing diisocyanates, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, 3,3-bischloromethyl ether 4,4'-diphenyldiisocyanate, trimethylhexamethylene diisocyanate. 1,4-diisocyanatobutane, 1,2-diisocyanatododecane and dimer fatty acid diisocyanate.

Other suitable commercially-available polyisocyanates include LUPRANATE M20 (polymeric methylene diphenyl diisocyanate, "PMDI" commercially available from BASF containing isocyanate group "NCO" 31.5 wt %), where the average n is 0.7; PAPI 27 (PMDI commercially available from Dow Chemical having an average molecular weight of 340 and containing NCO 31.4 wt %) where the average n is 0.7; MONDUR MR (PMDI containing NCO at 31 wt % or greater, commercially available from Covestro AG) where the average n is 0.8; MONDUR MR Light (PMDI containing NCO 31.8 wt %, commercially available from Covestro AG) where the average n is 0.8; MONDUR 489 (PMDI commercially available from Covestro AG containing NCO 30-31.4 wt %) where the average n is 1.0; poly[(phenylisocyanate)-co-formaldehyde] (Aldrich Chemical, Milwaukee, Wis.), other isocyanate monomers such as DESMODUR N3200 (poly(hexamethylene diisocyanate) commercially available from Covestro AG), and TAKENATE D110-N (xylene diisocyanate adduct polymer commercially available from Mitsui Chemicals corporation, Rye Brook, N.Y., containing NCO 11.5 wt %).

In particular embodiments, an exemplary isocyanate has the following structure:

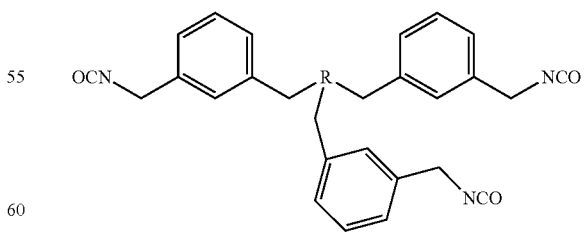

or its structural isomer, Representative isocyanates are TAKENATE D-110N (an isocyanate based on xylene diisocyanate commercially available from Mitsui), DESMODUR L75 (an isocyanate base on toluene diisocyanate commercially available from Covestro AG), and DESMODUR IL (another isocyanate based on toluene diisocyanate commercially available from Covestro AG).

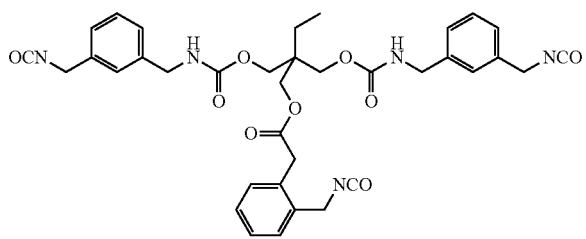

TAKENATE D-110N

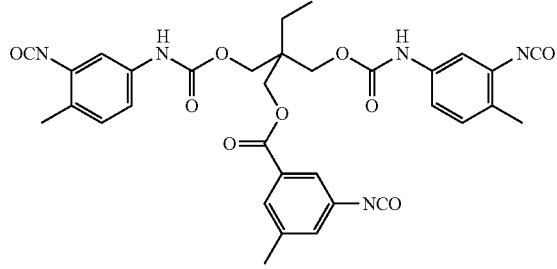

DESMODUR L75

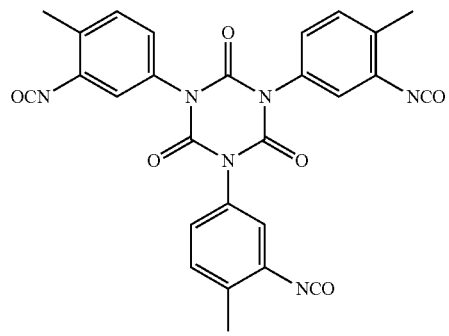

DESMODUR IL

In some embodiments, the isocyanate component used in the preparation of the microcapsules is a single isocyanate. In other embodiments, mixtures of isocyanates are employed. Such mixtures include wholly aliphatic isocyanates, wholly aromatic isocyanates and combinations of at least one aliphatic isocyanate and at least one aromatic isocyanate. Additionally, as noted above, suitable isocyanates include their respective dimers, trimers and biurets as well as oligomers and prepolymers, especially oligomers and prepolymers of the aforementioned isocyanates and diols, triols, diamines, triamines and/or other polyfunctional compounds reactive with the isocyanate groups in which at least one, preferably at least two of the reactive groups of said compounds are reacted with and thereby carry an isocyanate. All of these isocyanates and their adducts and the like are well known.

The average molecular weight of certain isocyanates useful in this invention varies from 250 to 1000 Da and preferably from 275 to 500 Da. In general, the range of the isocyanate concentration in the composition of this invention varies from 0.1% to 10%, preferably from 0.1% to 8%, more preferably from 0.2 to 5%, and even more preferably from 1.5% to 3.5%, all based on the total capsule composition.

More examples of suitable isocyanates can be found in PCT 2004/054362; EP 0 148149; EP 0 017 409 B1; U.S. Pat. Nos. 4,417,916, 4,124,526, 5,583,090, 6,566,306, 6,730,635. PCT 90/08468, PCT WO 92/13450, U.S. Pat. Nos. 4,681,806, 4,285,720 and 6,340,653.

Amine/Aminating Agent

The third wall forming component of microcapsules of the present teaching is the amine reactant or aminating agent. Especially preferred amine reactants are the aminosilanes, amino-(meth)acrylates, and amine radical initiators.

Amino silanes are well known and widely available. They are generally described by the following general formula

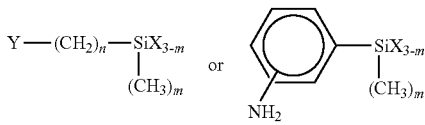

in which Y represents a substituted or unsubstituted amino group and each X is independently an alkoxy or acyloxy moiety with a maximum of 8, preferably 6, carbon atoms (which if desired, is interrupted by oxygen atoms), an amine or a halogen; m can assume the values 0 or 1 or 2, and n the values 1 or 2 or 3: most preferably, X is an alkoxy. Suitable substituents for the amino group can be alkyl moieties of 1 to 8 carbon atoms, acetyl moieties, and aryl moieties, especially, the phenyl moiety, cycloalkyl moieties, and alkylamino moieties such as —$CH_2CH_2NH_2$. The amino group can also be in the form of a quaternary ammonium salt. Exemplary silanes for use in the practice of the present teaching include, but are not limited to, gamma-aminopropyltrimethoxy-silane, gamma-amino-propyltriethoxysilane, gamma-aminopropylmethyldiethoxy-silane, gamma-amino-propyl-methyldimethoxy-silane, N-amino-ethylaminopropyl-trimethoxysilane, aminophenyl-trimethoxysilane, N-(2-amino-ethyl)-3-aminopropyl-methyl-dimethoxysilane, N-(2-amino-ethyl)-3-aminopropylmethyl-diethoxysilane, N-(2-amino-ethyl)-3-aminopropylmethyl-trimethoxysilane, N-(2-aminoethyl)-3-aminopropyl methyltriethoxysilane, Bis(3-trimethoxy-silylpropyl)amine, Bis(3-triethoxysilylpropyl)amine, 3-aminopropyl-dimethylmethyoxysilane, 3-amino-propyldimethyl-ethyoxysilane, diethylenetri-amino-propylmethyldimethoxysilane, diethylenetriaminopropyltrimethoxysilane, diethylamino-methyltriethoxysilane, N-(3-(trimethoxysilyl)-propylbutylamine, N-phenyl-3-amino-propyltrimethoxysilane, (N-phenyl-amino)-methyltriethoxysilane, (N-phenylamino)-methyltriethoxysilane, 3-(N-[dimethoxy-(methyl)silyl]propyl]cyclohexane amine, gamma-glycidyloxypropyltrimethoxysilane, and gamma-methacryloxypropyl-trimethoxysilane.

Amino-(meth)acrylates are also well known and widely available. They generally correspond to compounds of the following formulas:

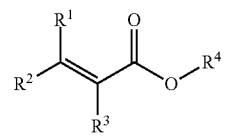

wherein at least one or $R^1$, $R^2$, $R^3$ and $R^4$ is or includes at least one amino functional group, which may be a primary or secondary amine, amide, or amidine, preferably —$NR^5R^6$, —$R^7$—$NR^5R^6$, —$C(=NR^8)NR^8R^8$ wherein each $R^5$, $R^6$, $R^7$, and $R^8$ is independently H or a $C_1$ to $C_{12}$, preferably a $C_1$ to $C_8$, alkyl, alkenyl, aryl or alkaryl group, preferably H or a $C_1$ to $C_3$ alkyl or alkenyl group or an amidine functional group of the formula $R^9$—C(=$NR^8$) $NR^8R^8$ wherein $R^8$ is as defined above and $R^9$ is a moiety having a functional group reactive with the hydroxy of the saccharide, e.g., an alkoxy group or alkoxy containing group; otherwise, $R^1$, $R^2$ and $R^4$ are independently H or a $C_1$ to $C_{12}$, preferably a $C_1$ to $C_8$, alkyl, alkenyl, aryl or alkaryl group, preferably H or a $C_1$ to $C_3$ alkyl or alkenyl group and $R^3$ is H or $CH_3$. Preferred amino functional (meth)acrylates are the alkyl amino acrylates, alkyl amino methacrylates, amino alkyl acrylates, amino alkyl methacrylates, di alkyl amino alkyl acrylates, di alkyl amino alkyl methacrylates, di amino alkyl acrylates, and di amino alkyl methacrylates including amino acrylate, ethyl amino acrylate, ethyl amino methacrylate, methyl 2-amino acrylate, methyl 2-amino methacrylate, ethyl 2-amino acrylate, ethyl 2-amino methacrylate, amino methacrylate, methyl amino methyl acrylate, methyl amino methyl methacrylate, methyl amino ethyl acrylate, methyl amino ethyl methacrylate, ethyl amino ethyl acrylate, ethyl amino ethyl methacrylate, methyl amino propyl acrylate, methyl amino propyl methacrylate, ethyl amino propyl acrylate, ethyl amino propyl methacrylate, methyl amino butyl acrylate, methyl amino butyl methacrylate, ethyl amino butyl acrylate, di ethyl aminobutyl methacrylate, di methyl amino methyl acrylate, di methyl amino methyl methacrylate, di methyl amino ethyl acrylate, di methyl amino ethyl methacrylate, di ethyl amino ethyl acrylate, di ethyl amino ethyl methacrylate, di methyl amino propyl acrylate, di methyl amino propyl methacrylate, di ethyl amino propyl acrylate, di ethyl amino propyl methacrylate, di methyl amino butyl acrylate, di methyl amino butyl methacrylate, di ethyl amino butyl acrylate, and diethyl aminobutyl methacrylate.

Alternatively, the amino functional contributing amine may be an initiator, especially a free radical initiator, containing one or more amino functional groups. Exemplary amine initiators are the azo initiators which are characterized as having the general formula:

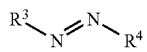

wherein $R^3$ and $R^4$ is as defined above provided that at least one of $R^3$ and $R^4$ is or contains an amino functional group which may be a primary, secondary, or tertiary amine, an amide, an amidine or a nitrile functional group, including cyano. Exemplary amine initiators include 2,2'-azobis (2-methylbutyronitrile), 1,1'-azobis cyclohexane carbonitrile, 2,2'-azobis (2-methylpropionamidine) dihydrochloride, 2,2'-Azobis(2-methylpropionamidine), 2,2'-Azobis(2-methylpropionitrile), 4,4'-Azobis (4-cyanovaleric acid) and Azodicarboxamide.

Core/Benefit Material

The capsules according to the present teaching are useful with a wide variety of capsule contents ("core materials" or "benefit agents") including, by way of illustration and without limitation, internal phase oils, solvent oils, phase change materials, lubricants, dyes, cleaning oils, polishing oils, flavorings, nutrients, sweeteners, chromogens, pharmaceuticals, fertilizers, herbicides, biological actives, scents, perfumes, fragrances, agricultural actives, essential oils, colorants, preservatives, antimicrobial actives, antifungal actives, herbicides, antiviral actives, antiseptic actives, antioxidants, biological actives, deodorants, antiperspirant actives, emollients, humectants, exfoliants, ultraviolet absorbing agents, corrosion inhibitors, silicone oils, waxes, bleach particles, fabric conditioners, malodor reducing agents, optical brighteners, perfume raw materials, such as alcohols, ketones, aldehydes, esters, ethers, nitriles, alkenes, fragrance solubilizers, preservatives, self-healing compositions, higher fatty acids, lipids, skin coolants, vitamins, sunscreens, glycerin, catalysts, silicon dioxide particles, brighteners, antibacterial actives, cationic polymers and mixtures of any two or more of the foregoing. Exemplary phase change materials useful as core materials include, by way of illustration and not limitation, paraffinic hydrocarbons having 13 to 28 carbon atoms, various hydrocarbons such n-octacosane, n-heptacosane, n-hexacosane, n-pentacosane, n-tetracosane, n-tricosane, n-docosane, n-heneicosane, n-eicosane, n-nonadecane, octadecane, n-heptadecane, n-hexadecane, n-pentadecane, n-tetradecane, n-tridecane. Additional or alternative phase change materials include crystalline materials such as 2,2-dimethyl-1,3-propanediol, 2-hydroxymethyl-2-methyl-1, 3-propanediol, acids of straight or branched chain hydrocarbons such as eicosanoic acid and esters such as methyl palmitate, fatty alcohols and mixtures thereof. Essential oils as core materials can include, for example, by way of illustration wintergreen oil, cinnamon oil, clove oil, lemon oil, lime oil, orange oil, peppermint oil and the like. Dyes can include fluorans, lactones, indolyl red, I6B, leuco dyes, all by way of illustration and not limitation. Other core materials include materials which alter rheology or flow characteristics of a product or extend shelf life or product stability.

As evident from the foregoing, the core materials include lipophilic/hydrophobic liquids as well as solid materials. Typically, though not necessarily, especially depending upon the core material itself, the core material is diluted with a diluent oil from 0.01 to 99.9 weight percent based on the combined weight of the diluent and core material in which it is dispersible or sufficiently soluble or miscible. In this regard, depending upon the specific core material and its use or purpose, the core material may be effective even at trace quantities, e.g., essential oils and fragrances. In following, the core material or benefit agent can be the majority or minority constituent encapsulated by the microcapsules.

In addition to the core material or benefiting agent, the oil phase, hence the microcapsule core, may also contain a partitioning modifier to aid encapsulation and retention of the core material or benefiting agent. The partitioning modifier can be the same material as the oil phase or diluent or can be different. The partitioning modifier can be selected from a larger group and can be further selected from the group consisting of oil soluble materials that have a C log P greater than from about 4, or from about 5, or from about 7, or even from about 11 and/or materials that also have a density higher than 1 gram per cubic centimeter.

Microcapsule Formation

The microcapsules of the present teaching are formed by two distinct processes, one in which the shell wall is a random cross-linked polymer of the wall-forming components and the other, the preferred embodiment, where the shell is structured or partially structured and employs, preformed or in-situ formed, amine modified polysaccharides. The microcapsules of each have certain benefits and advantages over traditional polysaccharide microcapsules as well as conventional polyurethane, polyurea and polyurethane/urea microcapsules, including those wherein a polysaccharide was present in the reaction mix as an emulsifiers/emulsion aid. Furthermore, those microcapsules according to the preferred embodiment have even better performance and properties, particularly with respect to degradability.

Briefly, the random polymer microcapsules are formed in a one-step oil-in water microencapsulation process wherein an oil phase comprising a core material and an isocyanate wall forming material, preferably a di- and/or poly-isocyanate, is dispersed in an aqueous phase comprising a polysaccharide wall forming material, preferably a hydrophobically modified polysaccharide, and a polyfunctional amine or amination agent reactive with both the polysaccharide and the isocyanate, which dispersion is then subjected to polymerization conditions whereby the isocyanate, the polysaccharide and the amine or aminating agent form a shell wall. Specifically, the random copolymer microcapsules are prepared by a) forming an oil phase of the core material and an isocyanate, especially a di- and/or poly-isocyanate monomer, dimer, trimer or biuret or a urethane or urea prepolymer or oligomer prepared therefrom, b) forming an aqueous phase of i) water, ii) a polysaccharide, especially a hydrophobically modified polysaccharide, iii) one or more di- or poly-functional amines and/or aminating agents, especially, one or more aminosilanes, amino-(meth)acrylates, and/or amine radical initiators or a combination of any two or more of the foregoing, and iv) optionally, though preferably, a caustic agent, especially caustic soda (as discussed below), and v) optionally, an emulsifier and/or initiator, c) dispersing/emulsifying the oil phase into the water phase under high shear agitation to form an oil-in-water emulsion comprising droplets of the oil phase dispersed in the water phase; and d) effecting polymerization of the wall forming materials, e.g., by heat and/or activation of the initiator, if present, thereby forming a polymer shell surrounding the droplets of the emulsified core material. The amino reactant has at least one amino functional group and is at least di-functional so as to be reactive with both the isocyanate and the polysaccharide: though the degree of functionality may be higher, generally no more than 6, preferably no more than 4, most preferably no more than 3. The at least one amino functional group can be selected from primary amine, secondary amine or an amidine group. Other suitable functional groups include hydroxy, alkoxy and vinylic groups. The relative amounts of the wall forming materials for the random polymer shell walls is such that the weight ratio of the wall forming polysaccharide content to isocyanate is generally from 40:60 to 99:1; preferably 50:50 to 99:1, more preferably from 60:40 to 98:2; most preferably from 70:30 to 98:2 and the mole ratio of the amine or aminating agent to the isocyanate of from 7:1 to 1:7, preferably from 5:1 to 1:5, more preferably 3:1 to 1:3: though, in the case of maltodextrins, especially low molecular weight maltodextrins, the mole ratio of amine or aminating agent to isocyanate may be up to 10:1, even up to 15:1, or more.

Notwithstanding the foregoing, the preferred microcapsules of the present teaching, the structured or partially structured microcapsules, are formed in either a one-step oil-in-water process or a two-step oil-in-water process. In the former, a preformed amine modified polysaccharide derived from the polysaccharide and a polyfunctional amine and/or another aminating agent is employed as the water phase wall forming material. In the latter, the amine modified polysaccharide is formed as a first step, generally without isolation, from the polysaccharide and the polyfunctional amine or aminating agent in the water phase or a portion thereof. While the amine modified polysaccharide may be prepared, before or after the oil phase is added to the water phase, it is preferably formed prior to the addition so as to avoid any substantial reaction between the isocyanate and the reactants for the amine modified polysaccharide: substantial reaction being evidenced by the formation of polyurethane and/or polyurea materials at the interface of the oil and water faces. If the amine modified polysaccharide is formed after the addition of the isocyanate, it is preferable that the reaction conditions for the formation of the amine modified polysaccharide are such as not to induce or induce any substantial reaction of the amine reactants with the isocyanate.

As noted, the two-step oil-in water microencapsulation process for forming the preferred microcapsules entails a first step comprising the preparation of an amine modified polysaccharide, preferably a hydrophobically modified polysaccharide, followed by a second step wherein a microcapsule wall is formed from the reaction of the amine modified polysaccharide and an isocyanate, preferably a di- or poly-isocyanate. Specifically, the two step process entails a) preparing a solution of the polysaccharide and the polyfunctional amine or aminating agent in water, b) forming an oil phase comprising a core material and an isocyanate wall forming material, especially a di- and/or poly-isocyanate, monomer, dimer, trimer or biuret or a urethane or urea prepolymer or oligomer prepared therefrom, c) either i) subjecting the water phase composition to reaction conditions whereby the amine modified polysaccharide is formed and subsequently dispersing the oil phase in the water phase or ii) dispersing the oil phase in the water phase and subsequently subjecting the water phase composition to reaction conditions whereby the amine modified polysaccharide is formed, and d) subjecting the dispersion to polymerization conditions whereby the isocyanate and the amine modified polysaccharide form a cross-linked polymer, e.g., by heat and/or activation of the initiator, if present, thereby forming a polymer shell surrounding the droplets of the emulsion. The water phase preferably includes a caustic agent, preferably caustic soda, to aid in the reaction of the polysaccharide and the aminating agent or reactant. Additionally, one may add an emulsifier and/or initiator to the water phase, either prior to or subsequent to the amination process. Further, if desired, one may add another or an additional polysaccharide to the water phase following the amination step, which additional polysaccharide may assist in the emulsification of the oil phase in the water phase and/or act as a further wall forming material in the second step.

As an alternative to the first step above, rather than form the amine modified polysaccharide in the whole of the water phase, one may do so in a water solution which is then added to the water phase or additional water may be added to it to form the actual water phase. In this instance, the reaction is more effective, speedier, and/or efficient given the higher concentration of the reactants and, if present, caustic. Additionally, one may elect to isolate or purify or partially isolate or purify the so formed amine modified polysaccharide to remove unwanted constituents, e.g., by solvent washes. Furthermore, it is desirable to at least partially isolate the amine modified polysaccharide to concentrate it for use in or as the water phase.

Generally speaking, the modified polysaccharide is prepared in the first step by reacting the polysaccharide with the amine or amino reactant. In forming the amine modified polysaccharide the mole ratio of the polysaccharide to amine or aminating agent is sufficient such that from 0.005 up to 8 mole percent, preferably from 0.01 up to 6 mole percent, more preferably from 0.05 up to 4 mole percent of the hydroxy groups of the polysaccharide have been substituted with a moiety having a free or reactive amino group, provided that, in the case wherein the amine modified polysaccharide is a maltodextrin, the amine modified polysaccharide has at least 1, preferably at least 2, more preferably at least 4 amino functional groups per molecule.

Amination of polysaccharide is preferably conducted in the presence of a caustic agent, typically an alkali aluminate or an alkali hydroxide, such as sodium aluminate, sodium hydroxide, potassium hydroxide and the like. The amount of the caustic agent is such that there will be approximately 0.3 moles of the caustic agent for each mole of the polyfunctional amine, typically mole ratios of 1:0.2 to 1:2, more typically 1:0.4 to 1:1.5. Although the caustic agent can be added initially, it is preferred to add the caustic agent to the reaction mix slowly during the amination process so as to better control the reaction.

As noted, the polysaccharide is preferably a hydrophobically modified polysaccharide, more preferably a starch, most preferably a hydrophobically modified starch. Although it is preferable to start with a hydrophobically modified polysaccharide, especially a hydrophobically modified starch, it is also to be appreciated that hydrophobic modification of the polysaccharide may be an additional step of the present process whereby the agent, especially the ester, employed to add hydrophobicity to the polysaccharide, is reacted with the polysaccharide prior to, concurrent with or subsequent to the amine modification of the polysaccharide. Such methods and appropriate reactions are well known. Exemplary modified starches and their preparation are described more fully in Amort et. al. (U.S. Pat. No. 4,540,777), which is incorporated herein by reference in its entirety.

Should it be desired, one may add additional polysaccharide (free of amine modification) to the water phase (after preparation of the amine modified polysaccharide, as appropriate). If additional polysaccharide is employed, it should be no more than 50 mole percent, preferably no more than 20 mole percent of the total polysaccharide component. Regardless, in forming the microcapsules, the weight ratio of the total wall forming polysaccharide content (e.g., the combination of the amine modified polysaccharide and the amine-free polysaccharide, if present,) to isocyanate is generally from 40:60 to 99:1; preferably 50:50 to 99:1, more preferably from 60:40 to 98:2; most preferably from 70:30 to 98:2.

Generally speaking, the one-step oil-in water microencapsulation process for forming the structured microcapsules comprises forming an oil phase comprising a core material and an isocyanate wall forming material, preferably a di- and/or poly-isocyanate, and dispersing the same in an aqueous phase comprising an amine modified polysaccharide wall forming material, preferably an amine modified hydrophobically modified polysaccharide, which dispersion is then subjected to polymerization conditions whereby the isocyanate and the amine modified polysaccharide form a cross-linked shell wall. Specifically, the one-step process entails a) forming an oil phase of the core material and an isocyanate, especially a di- and/or poly-isocyanate, monomer, dimer, trimer or biuret or a urethane or urea prepolymer or oligomer prepared therefrom, b) forming an aqueous phase of water and the amine modified polysaccharide, and, optionally, an emulsifier and/or initiator, c) dispersing/emulsifying the oil phase into the water phase under high shear agitation to form an oil-in-water emulsion comprising droplets of the oil phase dispersed in the water phase; and d) effecting polymerization of the wall forming materials, e.g., by heat and/or activation of the initiator, if present, thereby forming a polymer shell surrounding the droplets of the emulsion. The amine modified polysaccharide is preferably a starch, especially a hydrophobically modified starch, e.g., an esterified starch, which has been aminated or reacted to add amino functionality to the starch, most especially by reaction with one or more amino-silanes, amino-(meth) acrylates, and/or amine radical initiators or a combination of any two or more of the foregoing, as characterized above. The amine modified polysaccharide will typically have from 0.005 up to 8 mole percent, preferably from 0.01 up to 6 mole percent, more preferably from 0.05 up to 4 mole percent of the hydroxy groups of the polysaccharide substituted with a moiety having a free or reactive amino group, provided that, in the case wherein the amine modified polysaccharide is a maltodextrin, the amine modified polysaccharide has at least 1, preferably at least 2, more preferably at least 4 amino functional groups per molecule.

Optionally, one may add one or more additional polysaccharides or hydrophobically modified polysaccharides, which have not been modified to include amino functionality, to the water phase as an additional co-reactant and/or as an emulsifier. Regardless, in forming the microcapsules, the weight ratio of the total wall forming polysaccharide content (e.g., the combination of the amine modified polysaccharide and the amine-free polysaccharide, if present,) to isocyanate is generally from 40:60 to 99:1; preferably 50:50 to 99:1, more preferably from 60:40 to 98:2; most preferably from 70:30 to 98:2.

In each of the above-described processes, one may elevate the temperature of the water for the water phase to, perhaps 40° C. or so to aid in solubilization of the polysaccharide. Once the two phases are complete, the oil phase is dispersed in the water phase under high shear agitation to form an oil-in-water emulsion comprising droplets of the oil phase monomer dispersed in the water phase. Typically, a high shear mixer blade is used and the size of the microcapsules is controlled by adjusting the speed and timing of agitation during the emulsion formation. Smaller size dispersions are the result of faster agitation.

Once the proper or desired droplet size is attained, the mixture is heated to initiate the polymerization of the wall forming materials, typically to about 100° C., preferably to about 90° C. Although heat alone is typically sufficient to complete the microencapsulation process and wall formation, one can speed up wall formation by the addition of suitable polymerization initiators to the water phase. Suitable initiators include AIBN, sodium persulfate and benzoyl peroxide. When using initiators, the reaction temperature is elevated to whatever reaction temperature is appropriate for the initiator used. Additionally, as well recognized and known to those skilled in the art, one may use additional catalyst and/or pH adjustments to facilitate wall formation. In any event, at this point the speed of mixing is reduced, most preferably the high shear mixer blade is replaced with a stir bar or like, less aggressive mixing element. The elevated temperature is maintained with continued mixing for a sufficient time to complete the microcapsule wall formation. The microcapsules formed according to the present teaching may be recovered by any of the well-known and well-practiced methods in the art.

The thickness of the microcapsule wall is, in part, dependent upon the amount of the wall forming materials used. Generally, the wall forming material is from 0.1% to 40%, preferably from 0.1% to 20% based on the weight of the core composition to be encapsulated. Typical microcapsules formed in accordance with the present teaching will have a particle size of 0.1 to 150 microns, preferably from 0.5 to 100 microns, more preferably from 1 to 100 microns. Of course, different applications require larger or smaller particle sizes, even sized outside of the foregoing ranges.

As mentioned above, a number of other agents and additives may be present in the oil phase or water phase, particularly the latter, to aid in microcapsule formation and use. Exemplary additives include emulsifiers, deposition aids, initiators, pH adjusters, and the like.

Although the polysaccharide itself is found to aid in emulsification, it is often desirable to employ other emulsifiers. Such optional emulsifiers can be anionic, cationic, non-ionic and amphoteric emulsifiers. Generally preferred emulsifiers are the cationic and non-ionic emulsifiers, particularly those having poly (alkyl ether) units, especially polyethylene oxide units, with degrees of polymerization of the alkylene ether unit of greater than about 6. Preferred emulsifiers are those which significantly reduce the interfacial tension between the aqueous phase and oil phase, and thereby reduce the tendency for droplet coalescence. In this regard, generally the emulsifiers for use in the water phase for aiding in the oil in water emulsion or dispersion will have HLB values of from 8 to 20. Emulsifiers/surfactants of lower and higher HLB values that achieve the same objective may be employed.

For many emulsifiers, hydrophobic-lipophilic balance numbers (HLB) are reported in the literature and can be a useful guide in selection of the optional additional emulsifier.

| Emulsifier | HLB value |
| --- | --- |
| Glycerol monostearate | 3.8 |
| Diglycerol monostearate | 5.5 |
| Tetraglycerol monostearate | 9.1 |
| Succinic acid ester of monoglycerides | 5.3 |
| Diacetyl tartaric acid ester of monoglycerides | 9.2 |
| Sodium stearoyl-2-lactylate | 21.0 |
| Sorbitan tristerate | 2.1 |
| Sorbitan monostearate | 4.7 |
| Sorbitan monooleate | 4.3 |
| Polyoxyethylene sorbitan monostearate | 14.9 |
| Propylene glycol monostearate | 3.4 |
| Polyoxyethylene sorbitan monooleate | 15.0 |

As noted, typical oil in water emulsifiers generally have an HLB (hydrophilic-lipophilic balance) value of 8 to 20, preferably 8 to 16. HLB values below about 8 generally are used to promote the water in oil emulsions. Optional emulsifiers of all types are suitable for use in the practice of the present teaching, though it is to be appreciated, and those skilled in the art will readily recognize, that different systems, i.e., different oil phase compositions, will be better suited with one or more classes of emulsifiers than others.

Additionally, a deposition aid may be added to the water phase, before, during or after formation of the microcapsule. The deposition aid is typically present in an amount of 0.1-10%, preferably 0.1-7.5% more preferably 0.1-5% wt %, based on the microcapsule solution. Deposition aids typically coat the outer surface of the shell of the microcapsule and aid in their use and application. Deposition aids can be coated onto capsules or covalently bonded, employing functional groups to effect linkage as generally described in Universidade do Minho (WO 2006117702); Gross et al. (U.S. Pat. Publ. No. 20170296440); and Devan Micropolis (U.S. Pat. Publ. No. 20080193761)

Exemplary deposition aids include poly(meth)acrylate, poly(ethylene-maleic anhydride), polyamine, wax, polyvinyl-pyrrolidone, polyvinylpyrrolidone co-polymers, polyvinylpyrrolidone-ethyl acrylate, polyvinylpyrrolidone-vinyl acrylate, polyvinyl-pyrrolidone methacrylate, polyvinylpyrrolidone-vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinylpyrrolidone-/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof. Additional deposition aids include poly (acrylamide-co-diallyldimethylammonium chloride, poly (diallyldimethylammonium chloride, polyethylenimine, cationic polyamine, poly [(3-methyl-1-vinylimidazolium chloride)-co-(1-vinylpyrrolidone)], copolymer of acrylic acid and diallyldimethylammonium chloride, cationic guar, guar gum, an organopolysiloxane such as described in Gizaw et. al. (U.S. Pat. Publ. No. 20150030557), incorporated herein by reference.

Further, to aid in wall formation, one may add a variety of chemicals (borax, ammonium persulfate, epoxy resins, phosphate salts, etc.) to enhance cross-linked and to improve the physical and performance properties of the shell walls.

The microcapsules of the present teaching have, among other benefits, improved degradability due to the incorporation of the natural and bio-degradable polymer (polysaccharide) into the polyurethane/urea capsule wall. The microcapsules can be used dry or as a slurry of microcapsules, in coatings, as an additive to other materials, incorporated in or on fibers or textiles, or incorporated in or on polymeric materials, foams or other substrates. Optionally after microcapsule formation, the formed microcapsule can be isolated from the water phase or continuous phase, such as by decanting, dewatering, centrifuging, spray-drying, evaporation, freeze drying or other solvent removal or drying process.

The microcapsules of the invention can be incorporated dry, as an aqueous slurry, as a coating or as a gel into a variety of commercial products to yield novel and improved articles of manufacture, including incorporation into or onto foams, mattresses, bedding, cushions, added to cosmetics or to medical devices, incorporated into or onto packaging, dry wall, construction materials, heat sinks for electronics, cooling fluids, incorporated into insulation, used with lotions, incorporated into gels including gels for coating fabrics, automotive interiors, and other structures or articles, including clothing, footwear, personal protective equipment and any other article where use of the improved capsules of the invention is deemed desirable. Exemplary articles of manufacture include, but are not limited to soaps, surface cleaners, laundry detergents, fabric softeners, shampoos, textiles, coded dyes or pigments, paper products including carbonless record materials, tissues, towels, napkins, and the like, adhesives, wipes, diapers, feminine hygiene products, facial tissues, pharmaceuticals, deodorants, heat sinks, foams, pillows, mattresses, bedding, cushions, cosmetics and personal care products, medical devices, packaging, architectural coatings, surface treatments, pest repellents, paints, marine coatings, agricultural products including herbicides, fertilizers, and pesticides, coolants, wallboard, insulation, and the like. Blends of capsule populations can be useful, such as with differing sets of benefit agent, or even different wall formulations.

The microcapsules protect and separate the core material such as phase change material or fragrance or other core material or benefit agent, keeping it separated from the external environment. This facilitates design of distinct and improved articles of manufacture. The microcapsules facilitate improving flowability of encapsulated materials enhancing ease of incorporation into or onto articles such as foams, gels, textiles, various cleaners, detergents or fabric softeners. For example, with phase change benefit agents, the microcapsules help preserve the repeated activity of the phase change material and retain the phase change material to prevent leakage or infusion into nearby components when isolation of the microcapsules is desired, yet promote eventual degradation of such encapsulates or portions of the articles of manufacture.

Having described the general and specific aspects of the present teaching, attention is now directed to the following examples.

EXAMPLES

In the following examples, the abbreviations correspond to the following materials:

TABLE 1

| Name | Company/City | Chemical Description |
| --- | --- | --- |
| 2-AEMA | Sigma-Aldrich Inc., St. Louis, MO | 2-Aminoethyl methacrylate hydrochloride |
| 3-APTES | Gelest, Inc., Morrisville, PA | 3-aminopropyltriethoxysilane |
| CAPTEX 355 | Abitec, Columbus, OH | Caprylic/capric triglyceride |
| Caustic Soda | Hydrite Chemical Co., Brookfield, WI | Sodium hydroxide |
| DESMODUR W | Covesto AG | dicyclohexylmethane diisocyanate |
| GLOBE 10 | Ingredion, Westchester, IL | Maltodextrin (DE 10) |
| HI-CAP 100 | Ingredion, Westchester, IL | Octenyl Succinic Anhydride Starch |
| KPS | Sigma-Aldrich Inc., St. Louis, MO | Potassium persulfate |
| MONDUR MR LIGHT | Covesto AG | polymeric MDI (methylene diphenyl diisocyanate) |
| SR344 | Sartomer Company, Exton, PA | Polyethoxylated diacrylate |
| SR415 | Sartomer Company, Exton, PA | Ethoxylated trimethylolpropane triacrylate |
| TBAEMA | NovaSol North America Inc., Stoney Creek, ON, Canada | 2-(tert-butylamino) ethyl methacrylate |
| V-50 | Wako Specialty Chemicals, Richmond, VA | 2,2'-azobis(2-amidinopropane) hydrochloride |

The core oil used in the examples is an equal part blend of Captex 355 (triglycerides of caprylic/capric acid) and fragrance blend. The fragrance blend employed in the examples is an equal part blend of benzyl acetate, octanal, linalool, 2,6-dimethyl7-octen-2-ol, isobornyl acetate, linalyl acetate, butylphenyl methylpropional, isoamyl salicylate, and hexyl salicylate.

Example 1—Comparative Microencapsulation Process Illustrating Use of Unmodified OSA-Starch Microcapsules using an unmodified OSA-starch were prepared. A water phase solution containing 21 parts cool water and 3 parts HI-CAP 100 was mixed at 1,000 rpm. An oil phase solution was prepared containing 8 parts core oil and 1 part DESMODUR W. The water phase was pre-heated to 30° C. for 30 minutes prior to addition of the oil phase. The oil phase was added slowly to the water phase while mixing at approximately 2,500 rpm using a 4-tip milling blade. After 20 minutes, the milling blade was exchanged for a 3-blade propeller and mixing speed reduced to 475 rpm. The mixture was then heated from 30° C. to 90° C. over 30 minutes and heated at 90° C. for an additional 1,080 minutes.

Example 2—Low Level Aminosilane Modified Starch

An aminosilane modified starch was formed by adding 0.44 g. amino-propyltrimethoxysilane (3-ATPES) dropwise into 402 g water over a period of 10 minutes with stirring at room temperature. Thereafter 45.08 g HI-CAP 100 maize starch was added to the first solution over a period of 10 minutes with continued stirring. After approximately 30 minutes, once the starch was well dissolved, 0.4 g. of 21.5% caustic soda solution was gradually added and the solution heated to a temperature of 40° C. over a period of 30 minutes and held at that temperature for 120 minutes. The modified starch was isolated and collected by a series of lyophilization steps.

Example 3—High Level Aminosilane Modified Starch

A second aminosilane modified starch was formed by the same method as set forth in Example 2 except that the amount of 3-ATPES was increased to 4.43 g. and the amount of caustic soda increased to 4.01 g.

Example 4—Microencapsulation Process Illustrating Use of Aminosilane-Modified Starches Microcapsules were prepared according to the method of Example 1, replacing the HI-CAP 100 with the low level aminosilane modified starch of Example 2.

Example 5—Microencapsulation Process Illustrating Use of Aminosilane-Modified Starches Another set of microcapsules was prepared according to the method of Example 1, replacing the HI-CAP 100 with the high level aminosilane modified starch of Example 3.

Example 6—Amidine-Modified Starch

An amidine modified starch was formed by adding 274 g of HI-CAP 100 and 1,726 g of water to a jacketed reactor under 3-blade propeller mixing at 600 rpm for 30 minutes. 4.35 g of V-50 was then added to reactor under a nitrogen blanket. The solution was then heated to 89° C. over 167 minutes and held at a constant 89° C. for 43 minutes. The solution was then concentrated using a rotary evaporator at 20 mbar and 35° C. to a final concentration of 30% by mass.

Example 7—Microencapsulation Process Illustrating Use of Amidine-Modified Starch A water phase solution containing 18 parts water and 5 parts of the amidine modified starch prepared in Example 6 was mixed at 500 rpm for 10 minutes. An oil phase solution was prepared containing 14 parts core oil and 1 part MONDUR MR LIGHT. The oil phase was added slowly to the water phase while mixing at approximately 2,500 rpm using a 4-tip milling blade. After 30 minutes, the milling blade exchanged for a 3-blade propeller and mixing speed reduced to 500 rpm. The mixture was then heated from 20° C. to 50° C. over 30 minutes and heated at 50° C. for an additional 240 minutes.

Example 8—TBAEMA-Modified Maltodextrin

An amino acrylate modified maltodextrin was formed by forming a first water phase (WP1) with 270 g water and 3.6 g V-50 initiator, a second water phase (WP2) with 354 g water and 22 g GLOBE 10 maltodextrin from tapioca, and a third water phase (WP3) with 57 g water, 11 g SR415 and 4 g TBAEMA. WP1 was added to a jacketed reactor and heated from 40° C. to 55° C. over a period of 30 minutes and held at a constant 55° C. WP2 was preheated to 55° C. for 30 minutes after WP1 reached 55° C. After preheating, WP2 was added to WP1. 30 minutes after WP2 addition, WP3 was added drop-wise to the reactor over 20 minutes. The reactor temperature was maintained at 55° C. for an additional 740 minutes. A clear, light, amber-colored syrup was formed.

Example 9—Microencapsulation Process Illustrating Use of TBAEMA-Modified Maltodextrin Microcapsules using the TBAEMA-modified maltodextrin were prepared. A water phase solution containing 139 parts water and 7 parts TBAEMA-modified maltodextrin prepared in Example 8 was mixed at 500 rpm for 10 minutes. An oil phase solution was prepared containing 50 parts core oil and 1 part MONDUR MR LIGHT. The oil phase was added slowly to the water phase while mixing at approximately 3,250 rpm using a 4-tip milling blade. After 30 minutes, the milling blade was exchanged for a 3-blade propeller and mixing speed reduced to 250 rpm. The mixture was then heated from 20° C. to 50° C. over 30 minutes and heated at 50° C. for an additional 1,080 minutes.

Example 10-2AEMA-Modified Maltodextrin

A second amino acrylate modified maltodextrin was formed by forming a first water phase (WP1) with 23 g water and 0.3 g KPS initiator, a second water phase (WP2) with 164 g water and 20 g GLOBE 10 maltodextrin from tapioca, and a third water phase (WP3) with 63 g water, 11 g SR344 and 4 g 2AEMA. WP1 was added to a jacketed reactor and heated from 40° C. to 95° C. over a period of 30 minutes and held at a constant 95° C. WP2 was preheated to 55° C. for 30 minutes after WP1 reached 95° C. After preheating, WP2 was added to WP1. 30 minutes after WP2 addition, WP3 was added drop-wise to the reactor over 20 minutes. The reactor temperature was maintained at 95° C. for an additional 200 minutes. A clear, orange-colored syrup was formed.

Example 11—Microencapsulation Process Illustrating Use of 2AEMA-Modified Maltodextrin Microcapsules were prepared according to Example 9, replacing the TBAEMA-modified maltodextrin prepared in Example 8 with 2AEMA-modified maltodextrin prepared in Example 10.

Test Methods

Several test methodologies were performed on the microcapsules within the present invention. These test methods were for determining the particle size, free benefit agent, leakage into liquid fabric enhancer, and leakage in a hexane and ethanol solution. Test results are shown in table 3.

Batch Solids

The percent solids of the microcapsule batch were measured using a microwave and infrared moisture and solids analyzer (CEM Smart 6).

Median Volume Weighted Particle Size

The volume-weighted median particle size of the microcapsules is measured using an Accusizer 780A, made by Particle Sizing Systems, Santa Barbara Calif., or equivalent. The instrument is calibrated from 0 to 300 µm (micrometer or micron) using particle size standards (as available from Duke/Thermo-Fisher-Scientific Inc., Waltham, Mass., USA). Samples for particle size evaluation are prepared by diluting about 0.5 g of microcapsule slurry in about 10 g of de-ionized water. This dilution is further diluted using about 1 g of the initially diluted solution in about 20 g of water. Approximately 1 g of the most dilute sample is injected into the Accusizer and the testing initiated using the autodilution feature. The Accusizer should read more than 8.500 counts/second. If the counts are below 8,500 additional sample is added. The sample is autodiluted until below 9,200 counts/second was measured, then particle counting, and size analysis is initiated. After 2 minutes of testing, the Accusizer displays the median volume-weighted particle size. Particle sizes stated herein are on a volume weighted basis and are to be understood as median volume weighted particle size, ascertainable by the above procedure.

Percent Free Oil after Microencapsulation

Characterization of free oil in microcapsule suspension: 0.4-0.5 g of the microcapsule suspension is massed and mixed with 10 ml of hexane. The sample is mixed by vortexing at 3000 rpm for 10 seconds to leach the free oil from the microcapsule suspension and set aside for no more than one minute. An aliquot is removed from the hexane layer and filtered through a 0.45 µm syringe filter. The concentration of oil in the hexane is measured using an Agilent 7800 Gas Chromatograph (GC), Column: ZB-1HT (10 meter×0.32 mm×0.25 µm), Temp: 50° C. for 1 minute then heat to 270° C. @10° C./min, Injector: 275° C., Detector: 325° C., 2 µl injection.

Percent Leakage of Oil After 1 Week in Liquid Fabric Enhancer (LFE)

Characterization of the percent free oil after 1 week in liquid fabric enhancer: The percent activity of the microcapsule slurry is calculated as the grams of benefit agent divided by grams of microcapsule slurry. The mass of the slurry needed for testing is then calculated as 1.5 divided by the percent activity. 50 g of Downy Fabric Softener is added to a glass jar. The appropriate mass of slurry is massed and placed in the jar containing liquid fabric enhancer under stirring until homogenized. The jar is capped and placed in an oven at 35° C. for one week. After one week the amount of free oil is measured. 0.4-0.5 g of the microcapsule suspension is massed, mixed with 2 mL RO water, and vortexed at 1,000 rpm for 60 second. 10 ml of hexane is added and vortexed at 1,000 rpm for 60 seconds. The sample is allowed to rest 30 minutes. An aliquot is removed from the hexane layer and filtered through a 0.45 µm syringe filter. The concentration of oil in the hexane is measured using an Agilent 7800 Gas Chromatograph (GC), Column: ZB-1HT (10 meter×0.32 mm×0.25 µm), Temp: 50° C. for 1 minute then heat to 270° C. @10° C./min, Injector: 275° C., Detector: 325° C., 2 µl injection.

Determination of Release Properties of Oil (MT190)

Characterization of the release properties of the core oil were measured using the CIPAC MT190 test method. The percent free CAPTEX 355 after a one-hour extraction was normalized to the total concentration of CAPTEX 355 contained in the microcapsule slurry and reported in table 3.

TABLE 3

| Example | % Solids | Size (µm) | % Benefit Agent | Free Oil (RA) | LFE (RA) | MT190 % Actives |
|---------|----------|-----------|-----------------|---------------|----------|-----------------|
| 1  | 52.5  | 13.6 | 18.2 | 0.8 | 24.7 | 31.1 |
| 4  | 23.8  | 24.2 | 7.7  | 2.9 | 14.7 | —    |
| 5  | 37.2  | 16.2 | 12.0 | 2.4 | 38.5 | —    |
| 9  | 30.69 | 23.6 | 13.2 | 0.1 | 20.9 | 34.5 |
| 11 | 29.64 | 11.0 | 12.7 | 0.2 | 36.8 | 61.3 |

All documents cited in the specification herein are, in relevant part, incorporated herein by reference for all jurisdictions in which such incorporation is permitted. The citation of any publication is for its disclosure prior to the filing date and should not be construed as an admission that such publication is prior art or that the present invention is not entitled to antedate such publication by virtue of prior invention. To the extent that any meaning or definition of a term in this document conflicts with any meaning or definition of the same term in a document incorporated by reference, the meaning or definition assigned to that term in this document shall govern. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. No unclaimed language should be deemed to limit the invention in scope. Any statements or suggestions herein that certain features constitute a component of the claimed invention are not intended to be limiting unless reflected in the appended claims.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive variations and charges can be made by those skilled in the art without departing from the spirit and scope of the invention.

All documents cited in the specification herein are, in relevant part, incorporated herein by reference for all jurisdictions in which such incorporation is permitted. The citation of any publication is for its disclosure prior to the filing date and should not be construed as an admission that such publication is prior art or that the present invention is not entitled to antedate such publication by virtue of prior invention. To the extent that any meaning or definition of a term in this document conflicts with any meaning or definition of the same term in a document incorporated by reference, the meaning or definition assigned to that term in this document shall govern. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. All methods described herein can be performed in any suitable order unless otherwise indicated herein or otherwise clearly contradicted by context. The use of any and all examples, or exemplary language (e.g., "such as") provided herein, is intended to illuminate the present teaching and does not pose a limitation on the scope thereof. No unclaimed language should be deemed to limit the scope of the claims or teaching. Any statements or suggestions herein that certain features constitute a component of the claimed subject matter are not intended to be limiting unless reflected in the appended claims.

The principles, preferred embodiments, and modes of operation of the present teaching have been described in the foregoing specification. The teaching which is intended to be protected herein, however, is not to be construed as limited to the particular forms disclosed, since these are to be regarded as illustrative rather than restrictive variations and charges can be made by those skilled in the art without departing from the spirit and scope of the present teaching.

I claim:

1. A microcapsule comprising a core material and a shell encapsulating the core material wherein the shell comprises the reaction product of a) an amine modified polysaccharide and b) an isocyanate component comprising one or more di- and/or poly-isocyanates wherein i) the amine modified polysaccharide is characterized as having from 0.005 up to 8 mole percent of the hydroxy groups substituted with a moiety having a free or reactive amino group, and either A) the amine modified polysaccharide is the reaction product of a polysaccharide and one or more di- or poly-functional amines and/or aminating agents selected from one or more amino-silanes, one or more amino-(meth)acrylates, one or more amine free radical initiators or a combination of any two or more of the foregoing, wherein when the amine modified polysaccharide is a maltodextrin, the amine modified polysaccharide has at least 1 amino functional group per molecule, or B) the amine modified polysaccharide is or includes a maltodextrin having at least 4 amino functional groups per molecule, and ii) the weight ratio of the polysaccharide to isocyanate is from 40:60 to 99:1.

2. The microcapsule of claim 1 wherein the amine modified polysaccharide is the reaction product of a polysaccharide and one or more di- or poly-functional amines and/or aminating agents selected from one or more amino-silanes, one or more amino-(meth)acrylates or one or more amine free radical initiators or a combination of any two or more of the foregoing.

3. The microcapsule of claim 2 wherein the di- or polyfunctional amine is or includes an amino-(meth)acrylate.

4. The microcapsule of claim 1 wherein the amine modified polysaccharide is or includes a maltodextrin.

5. The microcapsule of claim 4 wherein the maltodextrin has at least 4 amino function groups and the free or reactive amino group of the polysaccharide is a primary amine, a secondary amine, an amide and/or an amidine group.

6. The microcapsule of claim 4 wherein the amine modified maltodextrin has at least 4 amino function groups and is the reaction product of a maltodextrin and one or more di- or poly-functional amines and/or aminating agents.

7. The microcapsule of claim 6 wherein the one or more di- or poly-functional amines and/or aminating agents is selected from one or more amino-silanes, one or more amino-(meth)acrylates or one or more amine free radical initiators or a combination of any two or more of the foregoing.

8. The microcapsule of claim 7 wherein di- or poly-functional amine is or includes an amino-(meth)acrylate.

9. The microcapsule of claim 1 wherein the amine modified polysaccharide is characterized as having from 0.01 up to 6 mole percent of the hydroxy groups substituted with a moiety having a free or reactive amino group.

10. The microcapsule of claim 1 wherein the amine modified polysaccharide is characterized as having from 0.05 up to 4 mole percent of the hydroxy groups substituted with a moiety having a free or reactive amino group.

11. The microcapsule of claim 1 wherein the amine modified polysaccharide is or includes a hydrophobically modified polysaccharide.

12. The microcapsule of claim 11 wherein the hydrophobically modified polysaccharide is an esterified starch.

13. The microcapsule of claim 1 wherein at least 50 mole percent of the isocyanates are di-isocyanates.

14. The microcapsule of claim 1 wherein at least 75 more percent of the isocyanates are di-isocyanates.

15. The microcapsule of claim 1 whose reactants further include up to 50 mole percent of one or more polysaccharides which have not been amine modified.

16. The microcapsule of claim 1 wherein the weight ratio of the total wall forming polysaccharide content to isocyanate is from 50:50 to 99:1.

17. The microcapsule of claim 1 wherein the weight ratio of the total wall forming polysaccharide content to isocyanate is from 70:30 to 98:2.

18. An oil-in water microencapsulation process comprising dispersing an oil phase composition comprising a core material and an isocyanate wall forming material comprising one or more di- or poly-isocyanates, in an aqueous phase composition and subjecting the dispersion to polymerization conditions; said aqueous phase composition, prior to subjecting the dispersion to polymerization conditions, comprising an amine modified polysaccharide wall forming material, whereby the isocyanate and the amine modified polysaccharide form a cross-linked shell wall encapsulating the core material; wherein i) the amine modified polysaccharide is characterized as having from 0.005 up to 8 mole percent of the hydroxy groups substituted with a moiety having a free or reactive amino group, and either A) the amine modified polysaccharide is the reaction product of a polysaccharide and one or more di- or poly-functional amines and/or aminating agents selected from one or more amino-silanes, one or more amino-(meth)acrylates or one or more amine free radical initiators or a combination of any two or more of the foregoing, wherein when the amine modified polysaccharide is a maltodextrin the amine modified polysaccharide has at least 1 amino functional group per molecule, or B) the amine modified polysaccharide is or includes a maltodextrin having at least 4 amino functional groups per molecule, and ii) the weight ratio of the polysaccharide to isocyanate is from 40:60 to 99:1.

19. The process of claim 18 wherein the amine modified polysaccharide is the reaction product of a polysaccharide and one or more di- or poly-functional amines and/or aminating agents selected from one or more amino-silanes, one or more amino-(meth)acrylates or one or more amine free radical initiators or a combination of any two or more of the foregoing.

20. The process of claim 19 wherein the di- or polyfunctional amine is or includes an amino-(meth)acrylate.

21. The process of claim 18 wherein the amine modified polysaccharide is or includes a maltodextrin.

22. The process of claim 21 wherein the maltodextrin has at least 4 amino function groups and the free or reactive amino group of the polysaccharide is a primary amine, a secondary amine, an amide and/or an amidine group.

23. The process of claim 21 wherein the maltodextrin has at least 4 amino function groups and the amine modified maltodextrin is the reaction product of a maltodextrin and one or more di- or poly-functional amines and/or aminating agents.

24. The process of claim 23 wherein the one or more di- or poly-functional amines and/or aminating agents is selected from one or more amino-silanes, one or more amino-(meth)acrylates or one or more amine free radical initiators or a combination of any two or more of the foregoing.

25. The process of claim 24 wherein di- or poly-functional amine is or includes an amino-(meth)acrylate.

26. The process of claim 18 wherein the amine modified polysaccharide is characterized as having from 0.01 up to 6 mole percent of the hydroxy groups substituted with a moiety having a free or reactive amino groups.

27. The process of claim 18 wherein the amine modified polysaccharide is characterized from 0.05 up to 4 mole percent of the hydroxy groups substituted with a moiety having a free or reactive amino group.

28. The process of claim 18 wherein the amine modified polysaccharide is or includes a hydrophobically modified polysaccharide.

29. The process of claim 28 wherein the hydrophobically modified polysaccharide is an esterified starch.

30. The process of claim 18 wherein at least 50 mole percent of the isocyanates are di-isocyanates.

31. The process of claim 18 wherein at least 75 more percent of the isocyanates are di-isocyanates.

32. The process of claim 18 whose reactants further include up to 50 mole percent of one or more polysaccharides which have not been amine modified.

33. The process of claim 18 wherein the weight ratio of the total wall forming polysaccharide content to isocyanate is from 50:50 to 99:1.

34. The process of claim 18 wherein the weight ratio of the total wall forming polysaccharide content to isocyanate is from 70:30 to 98:2.

35. The process of claim 18 further comprising, as preliminary steps, a) preparing an aqueous solution of a polysaccharide and one or more di- and/or polyfunctional amines or aminating agents selected from one or more aminosilanes, one or more amino-(meth)acrylates or one or more amine free radical initiators or a combination of any two or more of the foregoing, b) reacting the polysaccharide and the di- and/or polyfunctional amine(s) or aminating agent(s) to form the amine modified polysaccharide and c) either i) isolating the amine modified polysaccharide and using it to form the aqueous phase composition or ii) employing the reaction solution as the aqueous phase composition.

36. The process of claim 35 wherein the mole ratio of the amine or aminating agent to polysaccharide is from 7:1 to 1:7, wherein when the polysaccharide is a maltodextrin, the mole ratio may be up to 15:1.

\* \* \* \* \*